United States Patent
Sugiyama et al.

(10) Patent No.: US 9,902,857 B2
(45) Date of Patent: Feb. 27, 2018

(54) QUINACRIDONE PIGMENT OF LOW AMINE CONTENT AND METHOD FOR PRODUCING SAME

(71) Applicant: DIC Corporation, Tokyo (JP)

(72) Inventors: Kazuhiro Sugiyama, Sakura (JP); Kengo Yasui, Kamisu (JP); Kozue Sunouchi, Kamisu (JP)

(73) Assignee: DIC Corporation, Tokyo (JP)

(*) Notice: Subject to any disclaimer, the term of this patent is extended or adjusted under 35 U.S.C. 154(b) by 0 days.

(21) Appl. No.: 15/037,157

(22) PCT Filed: Oct. 23, 2014

(86) PCT No.: PCT/JP2014/078194
§ 371 (c)(1),
(2) Date: May 17, 2016

(87) PCT Pub. No.: WO2015/093144
PCT Pub. Date: Jun. 25, 2015

(65) Prior Publication Data
US 2016/0280924 A1    Sep. 29, 2016

(30) Foreign Application Priority Data

Dec. 19, 2013 (JP) ................. 2013-262457

(51) Int. Cl.
| | | |
|---|---|---|
| C09B 48/00 | (2006.01) |
| C09B 67/54 | (2006.01) |
| C09D 11/037 | (2014.01) |
| C09D 11/322 | (2014.01) |
| C09B 67/22 | (2006.01) |
| C09D 7/00 | (2018.01) |
| G03G 9/09 | (2006.01) |
| C07D 221/18 | (2006.01) |

(52) U.S. Cl.
CPC .......... *C09B 48/00* (2013.01); *C09B 67/0033* (2013.01); *C09B 67/0036* (2013.01); *C09B 67/0096* (2013.01); *C09D 7/007* (2013.01); *C09D 11/037* (2013.01); *C09D 11/322* (2013.01); *G03G 9/0922* (2013.01); *C07D 221/18* (2013.01)

(58) Field of Classification Search
CPC .............. C09B 48/00; C09B 671/0096; C09B 671/0033; C09B 671/0036; C09D 11/037; C09D 11/322; C09D 7/007; C07D 221/18; G03G 9/0922
See application file for complete search history.

(56) References Cited

U.S. PATENT DOCUMENTS

| 5,659,036 A * | 8/1997 | Maki | C07C 227/22 546/49 |
|---|---|---|---|
| 5,783,723 A * | 7/1998 | Campbell | C07C 67/343 546/58 |
| 5,817,817 A * | 10/1998 | Maki | C07C 227/22 546/49 |
| 8,167,793 B2 * | 5/2012 | Scott | A61B 1/00009 600/109 |
| 8,252,207 B2 * | 8/2012 | Namba | B41M 5/0023 252/511 |
| 8,466,219 B2 * | 6/2013 | Plueg | C08F 8/32 524/272 |
| 8,519,020 B2 * | 8/2013 | Aida | C09D 11/322 523/160 |
| 8,580,878 B2 * | 11/2013 | Hauck | B29C 45/14688 523/160 |
| 8,597,420 B2 * | 12/2013 | Iftime | H01F 1/0054 106/31.6 |
| 8,604,251 B2 * | 12/2013 | Berens | C07C 45/63 522/113 |
| 2008/0035965 A1 | 2/2008 | Hayashi et al. | |

FOREIGN PATENT DOCUMENTS

| CN | 1154387 A | 7/1997 |
|---|---|---|
| CN | 1283655 A | 2/2001 |
| JP | 07-126545 A | 5/1995 |
| JP | H07126545 A | 5/1995 |
| JP | 07-173408 A | 7/1995 |
| JP | 08-209008 A | 8/1996 |
| JP | 2002-146224 A | 5/2002 |
| JP | 2008-072090 A | 3/2008 |

OTHER PUBLICATIONS

International Search Report dated Jan. 20, 2015, issued for PCT/JP2014/078194.

\* cited by examiner

*Primary Examiner* — D Margaret M Seaman
(74) *Attorney, Agent, or Firm* — Locke Lord LLP

(57) ABSTRACT

Provided are a quinacridone pigment having a low content of a primary aromatic amine, a method for producing the same, and also a gravure and flexo ink, a colorant for plastic, a paint, a lithographic ink, a toner, or an ink-jet ink using the pigment. The quinacridone pigment having a low primary aromatic amine content is provided by washing a quinacridone pigment with at least one solvent selected from water and an organic solvent, or by adding an oxidizing agent to a pigment slurry including a quinacridone pigment and at least one solvent selected from water and an organic solvent to oxidatively decompose the aromatic amine.

5 Claims, No Drawings

QUINACRIDONE PIGMENT OF LOW AMINE CONTENT AND METHOD FOR PRODUCING SAME

FIELD OF INVENTION

The present invention relates to a highly safe quinacridone pigment with a low content of a specific primary aromatic amine (PAA) which is harmful to the human body, and a production method thereof.

BACKGROUND ART

Quinacridone pigment, known as an organic pigment, is a high weather resistant pigment showing a wide range of hues from violet to orange-yellow with red in the center, and has been widely used as a colorant in the range where gravure and flexo inks, colorants for plastics, paints, lithographic inks, toners, ink-jet inks and the like are available. From the practical aspect, severe requirements have been imposed thereto in terms of fastness characteristic and tint characteristic.

Among primary aromatic amines, there is a carcinogenetic kind, and its influence on the human body has recently been reported. Regulation of PAA in organic pigments used for various applications as a coloring material has been started in many countries. The regulation value thereof has conventionally been "less than 500 ppm", in accordance with AP(89)1 (EU Resolution on the Use of Colourants in Plastic Materials Coming into Contact with Food), BfR (the Federal Institute for Risk Assessment in Germany) Recommendation IX (Regulation for Colorants for Plastics and Other Polymers Used in Commodities), a self-imposed regulation by the Japan Hygienic Olefin and Styrene Plastics Association, and the like. However, carcinogenic o-anisidine was detected by a measurement method of PAA in paper napkin (EN645) established in 2008, and this triggered a movement to legislate PAA in paper napkin to 10 ppb or less (targeting the ultimate value of 0) in LUA (Landesuntersuchungsamt: a state laboratory in Germany). This value corresponds to a very severe value of 10 ppm or less in a pigment, and hence we pigment manufacturers have to promptly address the problem.

PTL 1 proposes a disazo pigment and a method for producing the disazo pigment, characterized by comprising, coupling a tetrazo solution of a benzidine compound with a coupler solution containing an acetoacetanilide compound to obtain a disazo pigment slurry, and treating the pigment slurry by adding a hypoiodite salt to the slurry and then precipitating fine particles of iodine under an acidic condition.

PTL 2 proposes a method for producing a disazo pigment with a low amine content, characterized by comprising, coupling a tetrazo solution of a benzidine compound with a coupler solution containing an acetoacetanilide compound in a stoichiometrically excess amount relative to the benzidine compound to obtain a disazo pigment slurry, and adding a halogen to the slurry, thereby treating the excess amount of the acetoacetanilide compound, and a disazo pigment obtained by the method.

PTL 3 proposes a method for producing a disazo pigment, characterized by comprising, coupling a tetrazo solution of a benzidine compound with a coupler solution containing an acetoacetanilide compound in a stoichiometrically excess amount relative to the benzidine compound to obtain a disazo pigment slurry, and adding an oxidizing agent to the slurry, thereby oxidatively decomposing the excess amount of the acetanilide compound.

CITATION LIST

Patent Literatures

PTL 1: JP-A-8-209008
PTL 2: JP-A-7-173408
PTL 3: JP-A-7-126545

SUMMARY OF INVENTION

Technical Problem

The related art documents described above relate to inventions of a disazo pigment and have no description about a primary aromatic amine in quinacridone. The inventions of the documents are thus not sufficient as a method for decreasing an amine content.

The halogen used in PTL 2 is a toxic gas and it is required to pay attention to gas leakage for safety concerns. Among others, strongly oxidative chlorine gas, which is colorless, requires careful attention. Bromine possibly undergoes an addition reaction of halogen to an aromatic compound under an environment exposed to light. In particular, the halogenation easily occurs with a phenol compound and the like, and therefore the color may be affected depending on the amount of by-products. In addition, the oxidation by halogen has to be conducted in an alkali condition. In cases of decomposing an anilide compound in an azo pigment, since the anilide compound is dissolved in an alkali condition, the solubility is increased to promote a decomposition reaction effectively. However, a quinacridone pigment contains an aromatic amine, and extraction of the aromatic amine compound incorporated in the pigment requires an acidic condition. Accordingly, an oxidizing agent that effectively functions in an acidic condition is needed.

PTL 3 provides a method in which a hypoiodite salt is added at a pH of 5.5 or lower. In this method, however, an alkali metal salt of iodide ion is produced as a reaction product, and when the salt remains in the pigment, the salt is oxidized by external air or sunlight to convert to iodine, which possibly affects the color.

The problem to be solved by the present invention is to provide a quinacridone pigment having a low primary aromatic amine content, and a method for producing the same, and further to provide a gravure and flexo ink, a colorant for plastics, a paint, a lithographic ink, a toner, or an ink-jet ink, using the same.

Solution to Problem

As a result of an intensive study in view of the above situation, the present inventors have found that a quinacridone pigment having a low content of a primary aromatic amine can be obtained by washing a quinacridone pigment with at least one solvent selected from water and an organic solvent or by adding an oxidizing agent to a pigment slurry including the quinacridone pigment and at least one solvent selected from water and an organic solvent to oxidatively decompose the aromatic amine, thereby accomplishing the present invention.

Specifically, the present invention provides the following inventions.

A quinacridone pigment, which has a content of a primary aromatic amine of 10 ppm or less.

The quinacridone pigment, wherein the quinacridone pigment comprises at least one selected from a compound represented by the general formula (I) and a solid solution of at least two compounds represented by the general formula (I):

[Chem. 1]

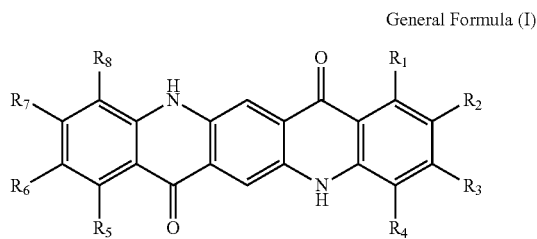

General Formula (I)

wherein in the formula, $R_1$ to $R_8$ each independently represent a hydrogen atom, a halogen atom, a C1 to C6 alkyl group or a C1 to C6 alkoxy group.

The quinacridone pigment, wherein the primary aromatic amine is represented by the general formula (II):

[Chem 2]

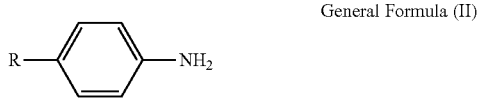

General Formula (II)

wherein in the formula, R represents a hydrogen atom, a halogen atom, a C1 to C6 alkyl group or a C1 to C6 alkoxy group.

A method for producing a quinacridone pigment, including washing a quinacridone pigment with at least one solvent selected from water and an organic solvent.

A method for producing a quinacridone pigment, including adding an oxidizing agent to a pigment slurry including a quinacridone pigment and at least one solvent selected from water and an organic solvent to oxidatively decompose the aromatic amine.

The method for producing a quinacridone pigment, wherein the oxidizing agent described above is at least one selected from nitrous acid and a salt thereof.

A gravure and flexo ink, a colorant for plastics, a paint, a lithographic ink, a toner, or an ink-jet ink, comprising the quinacridone pigment described above.

A gravure and flexo ink, a colorant for plastics, a paint, a lithographic ink, a toner, or an ink-jet ink, comprising a quinacridone pigment obtained by the method for producing a quinacridone pigment described above.

Advantageous Effects of Invention

The quinacridone pigment of the present invention contains a very low amount, 10 ppm or less, of a primary aromatic amine, and the invention has an especially notable technical effect of making it possible to provide a quinacridone pigment that has extremely low effects on the human body and has very high safety.

In addition, the invention of the method for producing a quinacridone pigment of the present invention has an especially notable technical effect of making it possible to easily decrease the primary aromatic amine in the quinacridone pigment described above.

DESCRIPTION OF EMBODIMENTS

Hereinunder, the present invention will be specifically described with reference to preferred embodiments.

The quinacridone pigment of the present invention is a quinacridone pigment having a primary aromatic amine content of 10 ppm or less.

The quinacridone pigment used in the present invention is an aromatic polycyclic organic pigment and is used as a versatile coloring material for a gravure and flexo ink, a colorant for plastics, a paint, a lithographic ink, a toner, an ink-jet ink, and the like.

As a method for producing the quinacridone pigment, a method has been known in which, for example, a succinylsuccinic acid diester compound and 2 molar equivalents of an aniline compound are subjected to dehydration condensation to obtain a 2,5-dianilino-3,6-dihydroterephthalic acid ester compound, and then the obtained compound is subjected to hydrolysis and oxidation to obtain a 2,5-dianilinoterephthalic acid compound, which is then subjected to intramolecular dehydrative cyclization in a strong acid, thereby obtaining unsubstituted quinacridone or a substituted quinacridone (acid cyclization method).

As the succinylsuccinic acid diester compound, although the alkyl group in the ester part thereof is not particularly limited, but dimethyl succinylsuccinate (DMSS) which is a methyl ester, or diethyl succinylsuccinate (DESS) which is an ethyl ester is generally used.

As the aniline compound, a compound represented by the general formula (II) is used:

[Chem 3]

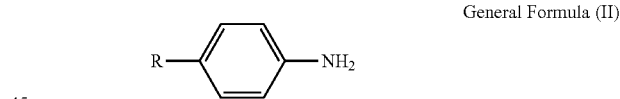

General Formula (II)

wherein in the formula, R represents a hydrogen atom, a halogen atom, a C1 to C6 alkyl group or a C1 to C6 alkoxy group.

The dehydration condensation step is conducted, for example, by heating the succinylsuccinic acid diester compound in an alcohol-based solvent in the presence of 2 to 4 mol of the aniline compound and 0.03 to 1.20 mol of an acid catalyst selected from hydrochloric acid, sulfuric acid, and hydrochloride of the aniline compound, per mole of the succinylsuccinic acid diester compound (see, U.S. Pat. No. 2,821,541, JP-A-11-158397).

The 2,5-dianilino-3,6-dihydroterephthalic acid ester compound obtained in the dehydration condensation step is a 2,5-dianilino-3,6-dihydroterephthalic acid ester or a derivative thereof having one or more substituent on at least one of two aniline rings, depending on aniline compound used. Examples of the derivative include a 2,5-di(4-methylanilino)-3,6-dihydroterephthalic acid ester, a 2,5-di(4-chloroanilino)-3,6-dihydroterephthalic acid ester, a 2,5-di(3-chloroanilino)-3,6-dihydroterephthalic acid ester, a 2,5-di(2-chloroanilino)-3,6-dihydroterephthalic acid ester, a 2,5-di(4- methoxyanilino)-3,6-dihydroterephthalic acid ester, and a 2-anilino-5-(4-methylanilino)-3,6-dihydroterephthalic acid ester.

The hydrolysis and oxidation step of the 2,5-dianilino-3,6-dihydroterephthalic acid ester compound is conducted by heating the compound in an alkaline alcohol-based solvent in the presence of oxygen (see, JP-A-2004-292333) or an oxidizing agent such as nitrobenzene and sodium nitrobenzenesulfonate (see, U.S. Pat. No. 3,388,149). The 2,5-dianilinoterephthalic acid compound obtained by the hydrolysis and oxidation step is the 2,5-dianilinoterephthalic acid or a derivative of the 2,5-dianilinoterephthalic acid, corresponding to the above mentioned 2,5-dianilino-3,6-dihydroterephthalic acid ester compound.

The intramolecular dehydrative cyclization step of the 2,5-dianilinoterephthalic acid compound is conducted in a dehydrating agent, in particular a strong acid, for example, a polyphosphoric acid, an ester of a polyphosphoric acid, or sulfuric acid. See, for example, U.S. Pat. No. 4,758,665, and an article entitled "quinacridone", S. S. Labana and L. L. Labana, Chemical Review, vol. 67, pp. 1 to 18 (1967). A polyphosphoric acid with a content of a phosphate group corresponding to $H_3PO_4$ of about 110 to 120% is especially suitable. In cases of using a polyphosphoric acid, a ratio of the polyphosphoric acid to a terephthalic acid intermediate is typically about 3:2 to about 10:1 (preferably 2:1 to 8:1). Although a highly viscous lump of the reaction product is produced when the ratio is low, such a low ratio is generally suitable from the viewpoint of the cost.

After the intermolecular dehydrative cyclization step is completed, a strongly-acidic molten substance is added to a liquid in which the quinacridone pigment is substantially insoluble, preferably water, a solvent which is miscible with water (for example, methanol, or another lower aliphatic alcohol), or a mixture thereof, to precipitate the quinacridone pigment (that is, "drowned" or subjected to precipitation separation). An excess amount of the liquid may be added to the acidic molten substance (for example, U.S. Pat. No. 3,265,699), but the present invention is preferably conducted by adding the acidic molten substance to the solvent (see, U.S. Pat. No. 4,100,162).

In the intramolecular dehydrative cyclization step, a mixture containing 2,5-dianilinoterephthalic acid and one or more of derivatives thereof, or a mixture containing two or more of 2,5-dianilinoterephthalic acid derivatives may be used. A method for using such a mixture is an especially advantageous method for obtaining a solid solution of quinacridone. A mixture obtained by combining 2,5-dianilinoterephthalic acid and/or a derivative thereof with a sufficiently purified quinacridone pigment (the quinacridone pigment is generally in a crude form) may also often be used.

As another method for producing a quinacridone pigment, a method is known in which a succinylsuccinic acid diester compound and an aniline compound is subjected to dehydration condensation to produce a 2,5-dianilino-3,6-dihydroterephthalic acid ester compound, the compound is subjected to intramolecular dealcoholization cyclization to produce a 6,13-dihydroquinacridone compound, and the compound is oxidized to obtain unsubstituted quinacridone or a substituted quinacridone compound (a heat cyclization method).

The intramolecular dealcoholization cyclization step of a 2,5-dianilino-3,6-dihydroterephthalic acid ester compound is conducted by heating, for example, in a nonreactive solvent whose boiling point is 225 to 300° C., at 225 to 300° C. for 45 minutes to 3 hours under blocking of oxygen. A 6,13-dihydroquinacridone compound obtained by the intramolecular dealcoholization cyclization step is the 6,13-dihydroquinacridone or a derivative of the 6,13-dihydroquinacridone, corresponding to the above-mentioned 2,5-dianilino-3,6-dihydroterephthalic acid ester compound.

The oxidation step of the 6,13-dihydroquinacridone compound is conducted by heating in an alkaline alcohol in the presence of oxygen or an oxidizing agent such as sodium nitrobenzenesulfonate and sodium polysulfide (for example, U.S. Pat. No. 2,821,529).

The quinacridone pigment obtained by the aforementioned method is a compound represented by the general formula (I) or a solid solution of two or three compounds represented by the general formula (I).

The primary aromatic amine contained in the quinacridone pigment is believed to be a remaining aniline compound which is a raw material of the quinacridone pigment, or a decomposition product or a by-product of the reaction intermediate or the reaction product. It is inferred that a part of reaction intermediates or reaction products is decomposed in the environment of a high temperature, a strong acid, or a strong alkali to produce the primary aromatic amine.

Accordingly, the primary aromatic amine is a compound represented by the general formula (II) and examples thereof include aniline, toluidine, chloroaniline, and methoxyaniline. The primary aromatic amine differs depending on the aniline compound which is a raw material for producing the quinacridone pigment.

As a method for decreasing the primary aromatic amines which have an harmful effect on the human body in the quinacridone pigment, a method of minimizing the remaining aniline compound in the 2,5-dianilino-3,6-dihydroterephthalic acid ester compound obtained by the dehydration condensation between the succinylsuccinic acid diester compound and the aniline compound, or a method of controlling the subsequent steps to inhibit the decomposition production of the primary aromatic amine is considered. Nevertheless, in a quinacridone pigment obtained by a typical synthesis method such as an acid cyclization method or a heat cyclization method, the primary aromatic amine of about several ten ppm or more is inevitably contained. Accordingly, it is required to decrease the primary aromatic amine in the produced quinacridone pigment by washing removal, decomposition removal, or the like of the primary aromatic amine. The amount of the primary aromatic amine contained in the resulting quinacridone pigment is preferably 10 ppm or less, and more preferably extremely close to 0 ppm.

The washing removal is a method in which the primary aromatic amine is extracted from the quinacridone pigment with a solvent such as water or an organic solvent, at room temperature or under heat, under pressure or at atmospheric pressure, thereby decreasing the primary aromatic amine.

The solvent usable for the washing can be arbitrary selected from solvents in which the aniline compound dissolves, and examples thereof include water containing an acid, an alcohol such as methanol, isopropanol and isobutanol, an ether such as tetrahydrofuran and diethylether, an aprotic polar solvent such as DMF and DMSO, a ketone such as acetone and methyl ethyl ketone, an ester such as ethyl acetate and propyl acetate, an aromatic hydrocarbon such as toluene and xylene, and the like. A mixed solvent thereof may be used, and the mixed solvent may be one of water and a water insoluble organic solvent.

As an acid contained in water, any acid can be used as long as it dissolves in water to make the pH lower than 7. The pH is preferably 5 or lower, and more preferably 3 or lower. Although a lower pH is preferred in terms of enhancing the solubility of the aniline compound, such an acid causes a problem of corrosion of the production facilities and hence a weak acid may be used by increasing the amount of the solvent or the number of the washing operations.

Although the extraction of the primary aromatic amine from the pigment depends also on the solubility of the solvent, the extraction speed can be increased by enhancing the mixing efficiency of the pigment and the solvent to loosen aggregated particles in order to extract the primary aromatic amine incorporated not only on the surface of the pigment particles but also in the aggregated particles. As means for enhancing the mixing efficiency, various means for mixing known in the art can be used. For example, a method using agitating blades that can give a higher diffusion coefficient as the liquid viscosity increases, a method in which a baffle is placed on a tank, and a method in which a dispersion is passed through a static mixer, can be used. Also by subjecting the dispersion to ultrasonic wave, dispersion of the pigment can be facilitated to enhance the extraction speed.

In the extraction of the primary aromatic amine from the pigment, the solvent needs to penetrate the pigment, and therefore the wettability of the pigment to the solvent has an effect on the extraction. Thus, a surfactant may be added to enhance the extraction speed. As the surfactant, depending on the kind of the pigment and solvent, any surfactant, such as an anionic surfactant, a cationic surfactant, and a nonionic surfactant which are generally used, can be selected.

Incidentally, since the pigment is a form of assembly of fine particles, the primary aromatic amine incorporated in the aggregate is difficult to be extracted even when using a common surfactant. Therefore, by the pigment dispersant being contained in a system of the pigment or the pigment dispersion, the extraction speed of the primary aromatic amine can be further enhanced. As the pigment dispersant, the above-mentioned surfactant plays the same role, but in addition to that, various pigment derivatives having a structure similar to the skeleton of the pigment and having a hydrophilic substituent may be used. As the pigment derivative suitable for the quinacridone pigment, a common known quinacridone derivative may be used, for example, a quinacridone sulfonic acid-based compound, and a phthalimidemethylated quinacridone can be exemplified (see, JP-A-2000-191974).

The decomposition removal which is another method for decreasing the primary aromatic amine is a method in which the quinacridone pigment is dispersed in a solvent such as water and an organic solvent, and an oxidizing agent or the like is optionally added to the dispersion, thereby decomposing the primary aromatic amine. The washing removal requires a large amount of water containing an acid or an organic solvent, and causes a problem of generating a large amount of waste. The discharge of the primary aromatic amine itself which has a harmful effect on human body is of course a problem. On the other hand, in the decomposition removal, the amount of solvent is an amount generally required for production, the amount of the oxidizing agent to be added is also very small, and the aniline compound can be converted into a less harmful compound. The decomposition removal is thus preferable from an industrial viewpoint.

Examples of the oxidizing agent usable for the decomposition include a nitrite salt such as sodium nitrite and potassium nitrite. Unlike those in PTL 2, these oxidizing agents can be handled in a form of solid or aqueous solution, are highly safe and do not affect hue of the pigment. In addition, these oxidizing agents can be incorporated in the cycle of nitrifying bacteria, and therefore, even when flowing into the wastewater, the oxidizing agents are expected to be treated in the bacterial process and thus impose a lower burden on the environment.

As the solvent usable for the decomposition, any one may be selected from solvents for use in washing and a mixture thereof also may be used. In terms of the solubility of the primary aromatic amine in water, as is the case in the washing removal, when using water, an acid is preferably added to make the pH 5 or lower, and more preferably 3 or lower. Since the nitrite salt which is an oxidizing agent has hydrophilicity, when a mixture of water and a water insoluble organic solvent is used as the solvent, most of the nitrite salt exists in an aqueous layer. On the other hand, as for many of aniline compounds, a larger amount thereof exists in an organic layer. In order to allow the nitrite salt and the aniline compound to react with each other, therefore, such an aniline compound has to be transferred into the aqueous layer from the organic layer quickly as much as possible by making the aqueous layer acidic. Accordingly, the aqueous layer needs to be acidic and the pH is preferably 5 or lower, more preferably 3 or lower.

The decomposition temperature is desirably a higher temperature from a viewpoint of enhancing the reaction speed, and the temperature may be a boiling point of the solvent or may be further increased in a pressure reactor such as an autoclave.

The reaction of the primary aromatic amine with the nitrite salt generally progresses quickly. However, since the content of the primary aromatic amine is generally 100 ppm or less, which is very low, the reaction is a thin system reaction and the reaction rate is largely affected by diffusion. Accordingly, in order to enhance the reaction rate, the same means for increasing the mixing efficiency as in the washing removal may be used.

In order to allow the primary aromatic amine to react with the nitrite salt, the primary aromatic amine has to be extracted from the pigment into a solvent, and therefore the same surfactant and/or pigment dispersant as in the washing removal may be used to enhance the reaction rate.

By enhancing the reaction rate of the primary aromatic amine with the nitrite salt as described above, the reaction rate can be improved. However, as the reaction time, a time period of 10 minutes to 10 hours, preferably of 10 minutes to 5 hours is generally required.

Next, the present invention will be described in detail with reference to examples and the like. Hereinunder, parts and percentages are given by mass, unless otherwise specified.

EXAMPLES

<Measurement Method of Primary Aromatic Amine>

In accordance with the AP(89)1 test method (ETAD212), 2 g of a pigment was placed in 50 ml plastic bottle, 3 ml of ethanol was added to wet the pigment, 30 ml of 1N-hydrochloric acid was added and the mixture was shaken by a paint conditioner for 30 minutes. The pigment was separated by filtration, and ml of the filtrate was mixed with 10 ml of a 4% ammonia/methanol solution to measure HPLC. From the calibration curve of PAA relative to the pigment, the PAA concentration was obtained. The detection limit of this test method depends on the sensitivity of HPLC, and from a result of repeated measurements of the blank, the detection limit was found to be 200 ppb in terms of the pigment.

Example 1

A solid solution crude pigment wet cake of unsubstituted quinacridone and 2,9-dimethylquinacridone was weighed by 50 g in terms of the pigment into a 1 L-autoclave container, 159 g of isobutanol and water in an amount to make the total mass 532 g were added, and the mixture was stirred to obtain a slurry. After the pH was adjusted to 7 with a 48% aqueous sodium hydroxide solution, the mixture was heated and stirred in the autoclave at 115° C. for 5 hours to produce a pigment. 92 g of water was added to dilute the mixture, 15% phosphoric acid was added at 70° C. to adjust the pH to 3, then 3 g of a 40% aqueous sodium nitrite solution was added, the pH was again adjusted to 3, and the mixture was stirred at 70° C. for 1 hour. Then, isobutanol was removed by distillation at normal pressure, and the obtained slurry was filtrated, dried and pulverized, whereby a pigment was obtained. In accordance with the test example, the total amount of aniline and p-toluidine in the solid solution pigment was measured, and the result was 6 ppm.

Example 2

A solid solution crude pigment wet cake of unsubstituted quinacridone and 2,9-dimethylquinacridone was weighed by 50 g in terms of the pigment into a 1 L-autoclave container, 159 g of isobutanol and water in an amount to make the total mass 532 g were added, and the mixture was stirred to obtain a slurry. After 15% phosphoric acid was added to adjust the pH to 5, 3 g of a 40% aqueous sodium nitrite solution was added, the pH was again adjusted to 3, and the mixture was heated and stirred in the autoclave at 115° C. for 5 hours to produce a pigment. Water (92 g) was added to dilute the mixture, then isobutanol was removed by distillation at normal pressure, and the obtained slurry was filtrated, dried and pulverized, whereby a pigment was obtained. In accordance with the test example, the total amount of aniline and p-toluidine in the solid solution pigment was measured, and the result was 10 ppm.

Example 3

A solid solution crude pigment wet cake of unsubstituted quinacridone and 2,9-dimethylquinacridone was weighed by 50 g in terms of the pigment into a 1 L-autoclave container, 159 g of isobutanol and water in an amount to make the total mass 532 g were added, and the mixture was stirred to obtain a slurry. After 15% phosphoric acid was added to adjust the pH to 3, 3 g of a 40% aqueous sodium nitrite solution was added, the pH was again adjusted to 3, and the mixture was heated and stirred in the autoclave at 115° C. for 5 hours to produce a pigment. Water (92 g) was added to dilute the mixture, then isobutanol was removed by distillation at normal pressure, and the obtained slurry was filtrated, dried and pulverized, whereby a pigment was obtained. In accordance with the test example, the total amount of aniline and p-toluidine in the solid solution pigment was measured, and the result was 3 ppm.

Example 4

An unsubstituted quinacridone pigment was obtained by the same operation as in Example 2 except that the solid solution crude pigment of the unsubstituted quinacridone and 2,9-dimethylquinacridone was changed to a unsubstituted quinacridone crude pigment. In accordance with the test example, the amount of aniline in the unsubstituted quinacridone pigment was measured, and the result was 2 ppm.

Example 5

A 3,10-dichloroquinacridone pigment was obtained by the same operation as in Example 2 except that the solid solution crude pigment of the unsubstituted quinacridone and 2,9-dimethylquinacridone was changed to a 3,10-dichloroquinacridone pigment (including 1,8-dichloroquinacridone and 1,10-dichloroquinacridone). In accordance with the test example, the amount of 3-chloroaniline in the 3,10-dichloroquinacridone pigment was measured, and the result was 9 ppm.

Example 6

A solid solution pigment of unsubstituted quinacridone and 2,9-dimethylquinacridone was weighed by 30 g into a 1 L-beaker, 450 g of a 1 N aqueous hydrochloric acid solution was added, and the mixture was stirred at room temperature for 1 hour to obtain a slurry. The obtained slurry was filtrated, dried and pulverized, whereby a pigment was obtained. In accordance with the test example, the total amount of aniline and p-toluidine in the pigment was measured, and the result was 6 ppm.

Example 7

A solid solution pigment of unsubstituted quinacridone and 2,9-dimethylquinacridone was weighed by 30 g into a 1 L-beaker, 450 g of methanol was added, and the mixture was stirred at room temperature for 1 hour to obtain a slurry. The obtained slurry was filtrated, dried and pulverized, whereby a pigment was obtained. In accordance with the test example, the total amount of aniline and p-toluidine in the pigment was measured, and the result was 1 ppm.

Comparative Example 1

A solid solution pigment of unsubstituted quinacridone and 2,9-dimethylquinacridone was obtained by the same operation as in Example 3 except for not adding the aqueous sodium nitrite solution. In accordance with the test example, the total amount of aniline and p-toluidine in the solid solution pigment was measured, and the result was 17 ppm.

Comparative Example 2

A unsubstituted quinacridone pigment was obtained by the same operation as in Example 4 except for not adding the aqueous sodium nitrite solution. In accordance with the test example, the amount of aniline in the pigment was measured, and the result was 19 ppm.

Comparative Example 3

A 3,10-dichloroquinacridone pigment was obtained by the same operation as in Example 5 except for not adding the aqueous sodium nitrite solution. In accordance with the test example, the amount of 3-chloroaniline in the pigment was measured, and the result was 42 ppm.

As described above, by washing a quinacridone pigment with at least one solvent selected from water containing an acid and an organic solvent, or by dispersing a quinacridone pigment in at least one solvent selected from water containing an acid and an organic solvent and adding an oxidizing agent to oxidatively decompose an aromatic amine, a quinacridone pigment in which the primary aromatic amine content has been decreased to an extremely low level, 10 ppm or less, can be obtained.

The invention claimed is:

1. A method for purifying quinacridone to obtain a quinacridone pigment which has a content of a primary aromatic amine of 10 ppm or less, comprising washing a quinacridone pigment with water containing an acid, the pH of which is lower than 7, and an organic solvent.

2. A method for purifying quinacridone to obtain a quinacridone pigment which has a content of a primary aromatic amine of 10 ppm or less, comprising adding an oxidizing agent to a pigment slurry including a quinacridone pigment and at least one solvent selected from water, water containing an acid, the pH of which is lower than 7, and an organic solvent to oxidatively decompose the aromatic amine.

3. The method for purifying quinacridone to obtain a quinacridone pigment according to claim 2, wherein the oxidizing agent is at least one selected from nitrous acid and a salt thereof.

4. A method for purifying quinacridone to obtain a quinacridone pigment according to claim 1, wherein
the primary aromatic amine is represented by the general formula (II):

[Chem 2]

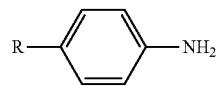

General Formula (II)

wherein in the formula, R represents a hydrogen atom, a halogen atom, a C1 to C6 alkyl group, or a C1 to C6 alkoxy group.

5. A method for purifying quinacridone to obtain a quinacridone pigment according to claim 2, wherein
the primary aromatic amine is represented by the general formula (II):

[Chem 2]

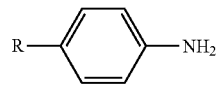

General Formula (II)

wherein in the formula, R represents a hydrogen atom, a halogen atom, a C1 to C6 alkyl group, or a C1 to C6 alkoxy group.

* * * * *